(12) United States Patent
Francisco, Jr.

(10) Patent No.: US 6,732,570 B2
(45) Date of Patent: May 11, 2004

(54) METHOD AND APPARATUS FOR MEASURING A FLUID CHARACTERISTIC

(75) Inventor: Edward E. Francisco, Jr., Paradise Valley, AZ (US)

(73) Assignee: Calibron Systems, Inc., Scottsdale, AZ (US)

( * ) Notice: Subject to any disclaimer, the term of this patent is extended or adjusted under 35 U.S.C. 154(b) by 0 days.

(21) Appl. No.: 10/410,076

(22) Filed: Apr. 9, 2003

(65) Prior Publication Data

US 2003/0200816 A1 Oct. 30, 2003

Related U.S. Application Data

(63) Continuation-in-part of application No. 09/930,636, filed on Aug. 15, 2001, now abandoned.
(60) Provisional application No. 60/298,576, filed on Jun. 14, 2001.

(51) Int. Cl.[7] .............................. G01N 9/00; G01F 1/20
(52) U.S. Cl. ..................... 73/32 A; 73/861.18
(58) Field of Search .................. 73/32 R, 32 A, 73/861.01, 861.18, 861.25, 861.26, 861.27, 861.28, 861.29, 861.3, 861.31

(56) References Cited

U.S. PATENT DOCUMENTS

| | | |
|---|---|---|
| 3,862,568 A | 1/1975 | Schlatter et al. |
| 4,262,523 A | 4/1981 | Stansfeld |
| 5,907,104 A | 5/1999 | Cage et al. |
| 5,965,824 A | 10/1999 | Kishiro et al. |
| 6,209,387 B1 | 4/2001 | Savidge |
| 6,227,059 B1 | 5/2001 | Schott et al. |
| 6,301,973 B1 | 10/2001 | Smith |

*Primary Examiner*—Helen C. Kwok
(74) *Attorney, Agent, or Firm*—Christie, Parker & Hale, LLP

(57) ABSTRACT

A tube through which fluid flows is installed in a fluid system. A piezoelectric driver is mounted on the exterior of the tube. A piezoelectric sensor is also mounted on the exterior of the tube. A feedback loop from the sensor to the driver is adapted to cause vibrations in the tube at its resonant frequency or a harmonic thereof. One or more strain gauges mounted on the exterior wall of the tube sense the strain exerted on the exterior wall by the pressure of the fluid flowing through the tube. A temperature sensor mounted on the exterior wall of the tube senses temperature. A microprocessor determines the density of the fluid flowing through the tube responsive to the piezoelectric sensor, temperature sensor and the one or more strain gauges. The one or more strain gauges comprise a bridge circuit. Strain gauges comprise two arms of the bridge circuit and temperature dependent resistors comprise the other two arms of the bridge. The output from the one or more strain gauges is used to correct the frequency reading given by the piezoelectric sensor.

27 Claims, 2 Drawing Sheets

METHOD AND APPARATUS FOR MEASURING A FLUID CHARACTERISTIC

RELATED APPLICATIONS

This application is a continuation-in-part of application Ser. No. 09/930,636 filed Aug. 15, 2001, now abandoned which claimed priority of U.S. provisional Application No. 60/298,576, filed Jun. 14, 2001, the disclosures of which are incorporated fully herein by this reference.

BACKGROUND OF THE INVENTION

This invention relates to measurement of a fluid characteristic and, more particularly, to a method and apparatus that compensates for pressure changes in the fluid being measured.

A known technique for measuring fluid characteristics such as fluid density and fluid flow rate is to pass the fluid through a tube and to set up vibrations in the tube. The resonant frequency of the tube depends upon the inherent characteristics of the tube and the fluid passing through the tube. For example, as the density of the fluid increases the effective mass of the tube also increases and the resonant frequency of the tube decreases. The stresses on the tube also affect the resonant frequency. These stresses are caused by various factors, the hydro-static pressure within or on the measurement tube, its temperature, and the whole densimeter's mounting hardware. For example, as the fluid pressure increases, the spring constant of the tube increases and the resonant frequency of the tube increases. In order to make the resonant frequency of the tube representative of the fluid density independent of pressure, the fluid pressure must be measured.

Typically, the fluid pressure is measured by inserting a pressure transducer inside the tube in contact with the fluid. As a result, the pressure transducer is exposed to the fluid, which can be intolerable if the fluid has destructive characteristics, i.e., if the fluid is corrosive or abrasive. Furthermore, in order to gain access to the pressure transducer for inspection, repair or replacement, the fluid system must be dismantled.

SUMMARY OF THE INVENTION

According to the invention, a tube is installed in a fluid system to ascertain changes in a characteristic of the fluid contained in the tube, such as resonant frequency. The fluid pressure in the tube is sensed by one or more strain gauges mounted on the exterior wall of the tube. The strain gauges measure the strain in the tube, which is proportional to the pressure exerted by the fluid on the tube. The measured strain is used to compensate for pressure induced changes in the tube's characteristics.

In one embodiment which senses fluid density, a tube through which fluid flows is installed in a fluid system. A piezoelectric or magnetic driver is mounted on the exterior of the tube. A piezoelectric or magnetic sensor is also mounted on the exterior of the tube. A feedback loop from the sensor to the driver is adapted to cause vibrations in the tube at its resonant frequency or a harmonic thereof. One or more strain gauges mounted on the exterior wall of the tube senses the strain exerted on the exterior wall by the pressure of the fluid flowing through the tube. A microprocessor determines the density of the fluid flowing through the tube responsive to the tube's motion, temperature sensor, and the one or more strain gauges.

In its preferred embodiment, the one or more strain gauges comprise a bridge circuit. Strain gauges comprise two arms of the bridge circuit and temperature dependent resistors comprise the other two arms of the bridge circuit. The output from the one or more strain gauges is used to correct the frequency reading given by the piezoelectric sensor.

BRIEF DESCRIPTION OF THE DRAWINGS

The features of specific embodiments of the best mode contemplated of carrying out the invention are illustrated in the drawings, in which.

DETAILED DESCRIPTION OF THE INVENTION

Figure 1:
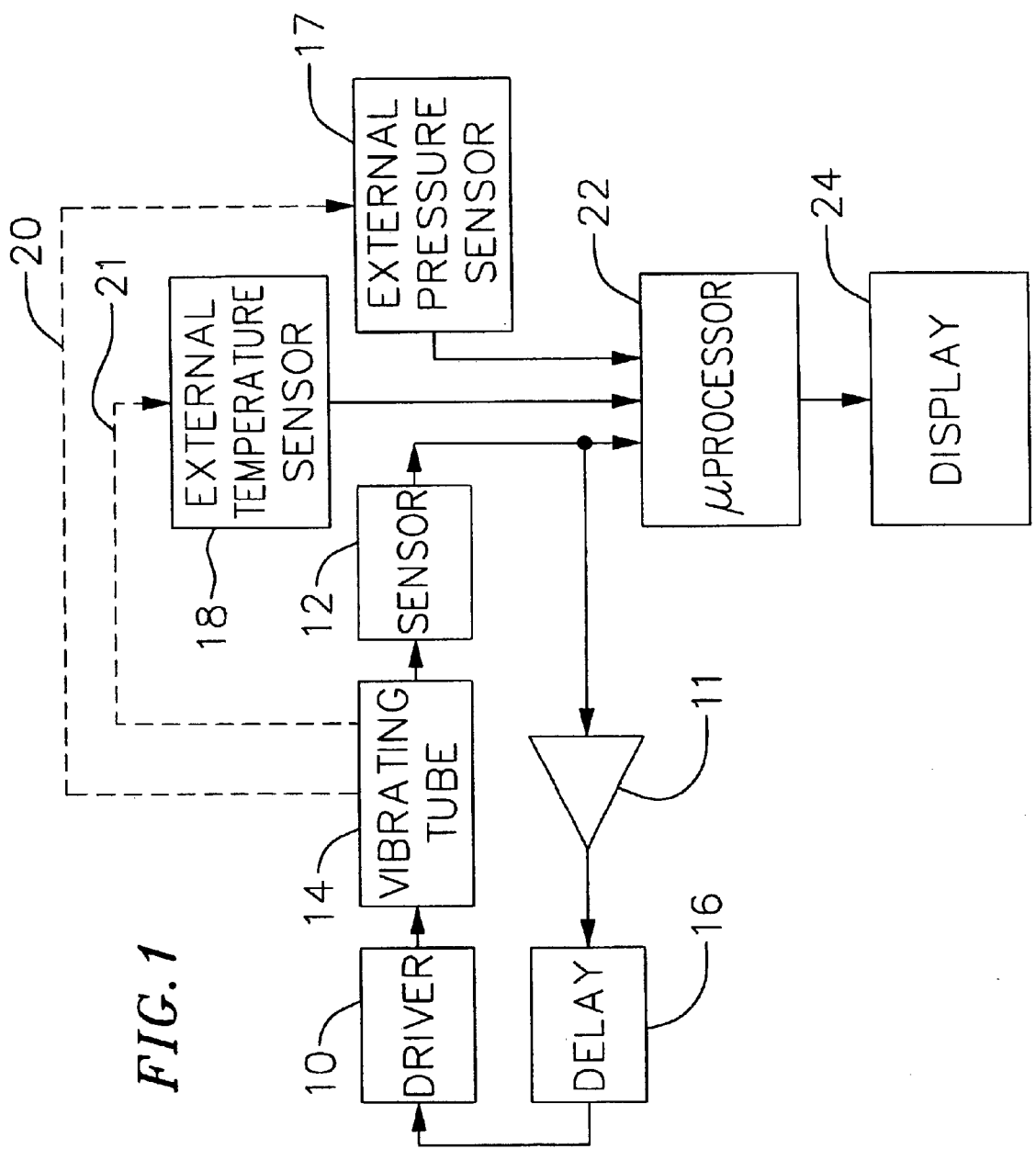
FIG. 1 is a schematic block diagram of a vibrating tube densimeter illustrating principles of the invention.

In FIG. 1 a driver 10 and a sensor 12 are mounted on the exterior wall of a vibrating tube 14. Tube 14 is installed in a flowing fluid system (not shown) such as a chemical plant, a refinery, or a food processing plant. Tube 14 could be directly installed in the fluid system so all the fluid flows through tube 14 or could be installed as a probe in the manner illustrated in U.S. Pat. No. 5,974,858, which issued on Nov. 2, 1999, the disclosure of which is incorporated herein by reference. The output of sensor 12 is coupled by an amplifier 11 to driver 10 in a feedback loop that also includes a delay 16. Typically, driver 10 and sensor 12 are piezoelectric or magnetic devices. By virtue of the feedback loop from sensor 12 to driver 10, tube 14 vibrates at its resonant frequency or a harmonic thereof. Amplifier 11 provides the power for these vibrations. The phase shift from the output of sensor 12 to the input of driver 10 depends in part on the relative circumferential positioning of driver 10 and sensor 12. The mode of vibration, i.e., axial or radial, depends upon the conditions established in the feedback loop such as the relative positioning of driver 10 and sensor 12. If tube 14 has a large diameter (e.g., larger than one inch), the resonant frequency in the radial direction is used to measure the density, because otherwise the tube must be too long to keep the resonant frequencies of 1500 to 4500 Hz. In this case, If tube 14 has a small diameter (e.g., one inch or less), resonant frequency in the axial direction is used to measure the density, because otherwise the tube must be too long, and typical resonant frequencies are in the range of 1000 to 1500 Hz. The described components are analogous to an electrical oscillator, the mass and spring constant of tube 14 are analogous to the tank circuit of the oscillator. Delay 16 is designed to create regenerative feedback. Delay 16 represents delay caused by the relative positioning of driver 10 and sensor 12 around the circumference of tube 14 and/or an electrical delay in the feedback loop. As is known in the art, the resonant frequency of tube 14 depends upon the tube's mass, spring constant, the density of the fluid traveling through tube 14, the temperature of the fluid inside the tube 14, and is also affected by the fluid pressure inside tube 14. A temperature sensor outside tube 14 senses the temperature of the fluid. Sensor 18 could be an off the shelf resistive temperature device (RTD) that changes resistance in a linear relationship to temperature. In the prior art, to compensate for fluid pressure an internal pressure sensor has been mounted inside the tube in contact with the fluid.

According to the invention, however, an external pressure sensor 17 is mounted on the outside wall of tube 14. As represented by a dashed line 20, pressure sensor 17 responds to the pressure of the fluid within tube 14. As represented by a dashed line 21, an external temperature sensor 18 responds to the temperature of tube 14, which is representative of the fluid temperature inside tube 14. The output of sensor 12, which represents the resonant frequency of tube 14 or a harmonic thereof, including the fluid contained therein, in the selected mode, the output of external pressure sensor 17, and the output of external temperature sensor 18 are coupled to the inputs of a microprocessor 22, which is programed to calculate the density of the fluid contained within tube 14. The calculated density can be read from a display 24.

Alternatively, the invention could be used to measure the density of a static fluid, i.e., a non-flowing fluid or the flow rate of fluid in a fluid system, as in a Coriolis meter.

Figure 2:
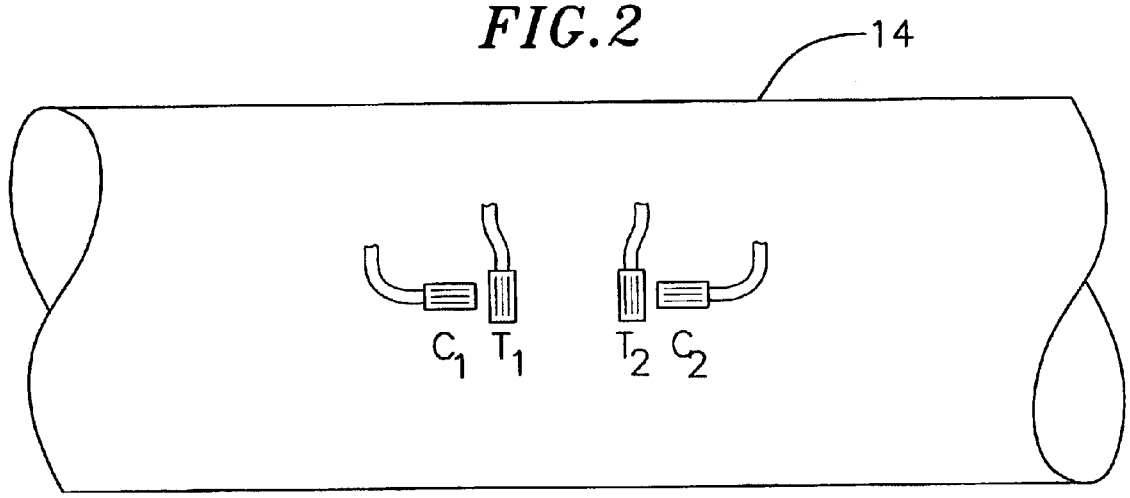
FIG. 2 is a diagram of a vibrating tube having temperature and pressure sensing elements mounted on the exterior wall of the tube.

FIG. 2 illustrates part of the exterior wall of vibrating tube 14 and pressure sensor 17 mounted thereon. As illustrated in FIG. 2, for vibration in a radial mode, a pair of circumferentially oriented strain gauges are mounted on the exterior sidewall of tube 14 to measure changes in the circumferential stress representative of the fluid pressure and a pair of axially oriented strain gauges are mounted on the exterior sidewall of tube 14 to compensate for temperature changes. For vibration in an axial mode (not shown), a pair of axially arranged strain gauges would be mounted on the exterior sidewall of tube 14 to measure changes in the axial stress representative of the fluid pressure and a pair of circumferentially oriented strain gauges would be mounted on the exterior sidewall of tube 14 to compensate for temperature changes. The strain gauges could be of the metal foil type.

Figure 3:
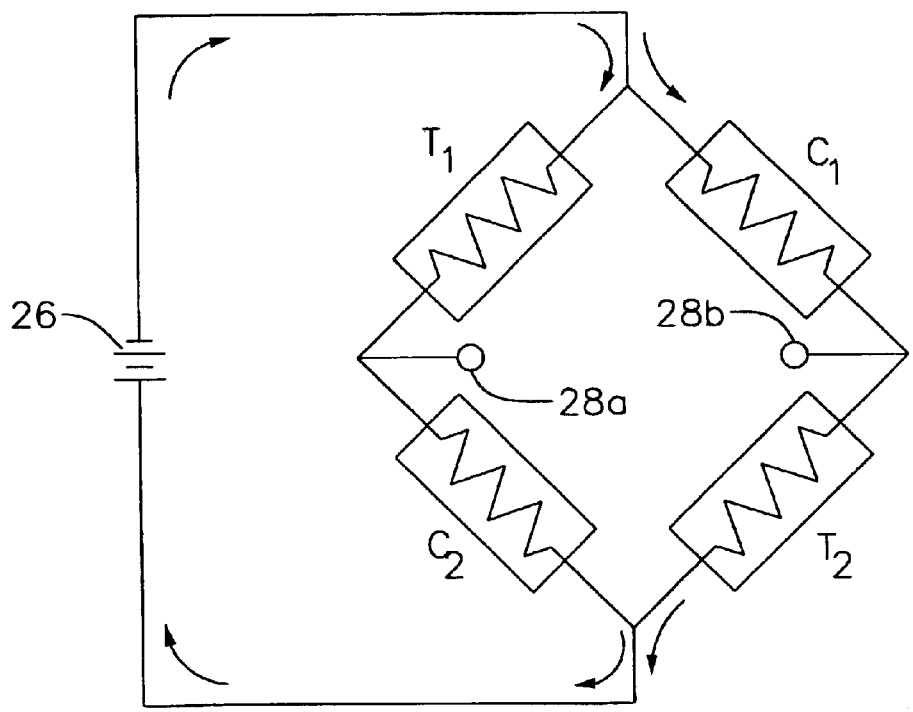
FIG. 3 is an electrical schematic diagram of the temperature and pressure sensing elements of FIG. 2. connected in a bridge circuit.

FIG. 3 illustrates the electrical circuit connections of the strain gauges for the mode represented in FIG. 2. Strain gauges $T_1$, and $T_2$ and strain gauges $C_1$ and $C_2$ comprise the arms of the bridge circuit. One terminal of a direct current bias source 26 is connected to the junction of strain gauges $T_1$, and $C_1$. The other terminal of bias source 26 is connected to the junction of strain gauges $T_2$ and $C_2$. The junction of strain gauges $T_1$ and $C_2$ comprises one output terminal 28$a$ of the bridge circuit. The junction of strain gauges $T_2$ and $C_1$ comprises the other output terminal 28$b$ of the bridge circuit. All the strain gauges are at the same temperature because they are mounted in close proximity to each other on the same heat conductive surface. As a result, the effect of temperature on the strain gauges is balanced by the bridge and thus the output of the bridge is independent of temperature.

One of a number of suitable algorithms is selected to calculate a pressure compensated density value. Microprocessor 22 is programmed to calculate the density of the fluid in tube 14 (whether flowing or stationary) from the outputs of sensors 12, 17, and 21. The presently preferred algorithm to calculate density is the following:

$$Dpt=DT+(DT \times Kp1 \times P)+(Kp2 \times P)+Kp3 \times P^2$$

In this algorithm, Dpt represents the calculated density, DT represents the temperature measured by sensor 18 in FIG. 1, P represents the pressure measured by the bridge circuit of FIG. 3, $P^2$ represents the measured pressure squared, and Kp1, Kp2, and Kp3 are constants derived by calibration. Preferably, the constants are determined by weighing a reference fluid over a range of known temperatures and pressures that will be encountered in the course of the measurements. (Typical reference fluids for this purpose are propylene glycol, ethylene glycol, propane, the fluid being measured, or another fluid that responds linearly to temperature and pressure changes.) First, the pressure is held constant while the temperature is varied and the measured resonant frequency data is recorded. Then, the temperature is held constant while the pressure is varied and the measured resonant frequency is data recorded. The constants are selected based on this data, so the calculated density, Dpt, equals the known density of the reference fluid at each pressure and temperature.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention. For example, instead of a bridge composed of strain gauges, a single strain gauge could be used, but this produces half the output signal amplitude of a full bridge, and is very temperature sensitive.

What is claimed is:

1. Apparatus for measuring density of a fluid comprising:

a hollow tube that contains the fluid;

means for inducing the tube to vibrate at the resonant frequency of the tube or a harmonic frequency thereof;

means for sensing the frequency of the vibrations;

means for sensing the strain in a wall of the tube; and means responsive to the frequency sensing means and the strain sensing means for calculating fluid density.

2. The apparatus of claim 1, in which the strain sensing means is located on the exterior surface of the tube out of contact with the fluid.

3. The apparatus of claim 1, in which the tube is straight.

4. The apparatus of claim 1, in which the inducing means causes the tube to vibrate axially.

5. The apparatus of claim 1, in which the inducing means causes the tube to vibrate radially.

6. The apparatus of claim 1, in which the inducing means comprises a piezoelectric or magnetic driver mounted on the tube, a piezoelectric or magnetic sensor mounted on the tube, a feedback loop connecting the sensor to the driver; and a delay in the feedback loop designed so the driver is in phase with the sensor.

7. The apparatus of claim 1, in which the frequency sensing means comprises a piezoelectric or magnetic sensor.

8. The apparatus of claim 1, in which the strain sensing means comprises a bridge circuit having first and second arms connected in series, third and fourth arms connected in series, a bias source connected between a junction of the first and third arms and a junction of the second and fourth arms, a first output terminal at a junction of the first and second arms, and a second output terminal at a junction of the third and fourth arms, the first and third arms comprising strain dependent resistors, and the second and fourth arms comprising temperature dependent resistors.

9. The apparatus of claim 1, in which the tube is installed in a flowing fluid system so the flowing fluid passes through the tube.

10. The apparatus of claim 8, in which the fluid characteristic is density and the calculating means calculates the density of the fluid.

11. The apparatus of claim 8, in which the fluid characteristic is flow rate and the calculating means calculates the flow rate of the fluid.

12. The apparatus of claim 1, additionally comprising means for displaying the calculated fluid characteristic.

13. The apparatus of claim 1, additionally comprising means for sensing the temperature of the fluid, the calculating means being partially responsive to the temperature sensing means to correct the calculated fluid characteristic for temperature changes.

14. The apparatus of claim 2, in which the inducing means comprises a piezoelectric driver mounted on the tube, a piezoelectric sensor mounted on the tube, a feedback loop connecting the sensor to the driver; and a delay in the feedback loop designed so the driver is in phase with the sensor.

15. The apparatus of claim 14, in which the frequency sensing means comprises a piezoelectric sensor.

16. The apparatus of claim 15, in which the strain sensing means comprises a bridge circuit having first and second arms connected in series, third and fourth arms connected in series, a bias source connected between a junction of the first and third arms and a junction of the second and fourth arms, a first output terminal at a junction of the first and second arms, and a second output terminal at a junction of the third and fourth arms, the first and third arms comprising strain dependent resistors, and the second and fourth arms comprising temperature dependent resistors.

17. The apparatus of claim 16, in which the tube is installed in a flowing fluid system so the flowing fluid passes through the tube.

18. The apparatus of claim 17, additionally comprising means for displaying the calculated fluid characteristic.

19. The apparatus of claim 18, in which the inducing means causes the tube to vibrate axially.

20. The apparatus of claim 18, in which the inducing means causes the tube to vibrate radially.

21. The apparatus of claim 19, in which the fluid characteristic is density and the calculating means calculates the density of the fluid.

22. The apparatus of claim 20, in which the fluid characteristic is density and the calculating means calculates the density of the fluid.

23. The apparatus of claim 19, in which the fluid characteristic is flow rate and the calculating means calculates the flow rate of the fluid.

24. The apparatus of claim 20, in which the fluid characteristic is flow rate and the calculating means calculates the flow rate of the fluid.

25. A densimeter comprising:
a tube through which fluid flows;
a piezoelectric driver mounted on an exterior surface of the tube;
a piezoelectric sensor mounted on an exterior surface of the tube;
a feedback loop from the sensor to the driver adapted to cause vibrations in the tube at the resonant frequency of the tube or a harmonic frequency thereof;
one or more strain gauges mounted on an exterior surface of the tube to sense strain exerted on the exterior wall by the pressure of fluid flowing through the tube; and
a microprocessor for determining the density of the fluid flowing through the tube responsive to the piezoelectric sensor and the one or more strain gauges.

26. A method for determining the density of a fluid flowing through a fluid system, the method comprising the steps of:
installing a straight tube in the fluid system so fluid flowing through the system also flows through the tube;
setting up vibrations having a frequency in the tube;
sensing the frequency of the vibrations;
sensing strain in the wall of the tube caused by the pressure of the fluid flowing through the tube; and
calculating the density of the fluid flowing through the tube from the sensed frequency and the sensed strain.

27. The method of claim 26, in which the calibration constants are derived by:
sensing the temperature of the fluid;
sensing the pressure of the fluid;
sensing the frequency of the vibrations;
measuring the densities of a known reference fluid over a range of temperatures with the pressure held constant;
measuring the densities of the known reference fluid over a range of pressures with the temperature held constant; and
selecting calibration constants based on the measured densities of the known reference fluid over the range of temperatures with the pressure held constant and the measured densities of the known reference fluid over the range of pressures with the temperature held constant.

* * * * *